United States Patent [19]
Hudlicky

[11] Patent Number: 5,200,516
[45] Date of Patent: Apr. 6, 1993

[54] SYNTHESIS OF SUGARS FROM SUBSTITUTED AND UNSUBSTITUTED ARENE DIOLS

[75] Inventor: Tomas Hudlicky, Blacksburg, Va.

[73] Assignee: Virginia Tech Intellectual Properties, Blacksburg, Va.

[21] Appl. No.: 802,943

[22] Filed: Dec. 6, 1991

Related U.S. Application Data

[63] Continuation-in-part of Ser. No. 480,891, Feb. 16, 1990, abandoned.

[51] Int. Cl.$^5$ .................. C07G 3/00; C07G 11/00; C07H 15/00; C07H 17/00
[52] U.S. Cl. ............................ 536/41; 127/34; 127/42; 536/18.5; 536/124
[58] Field of Search ............ 536/4.1, 18.5, 124; 127/34, 42

[56] References Cited

PUBLICATIONS

The Merck Index, 10th Edition, 1983, p. 3637, published by Merck & Co., Inc., Rahway, N.J., U.S.A.
Ballou, *J. Am. Chem. Soc.*, 1957, p. 165.
Gibson et al., *Biochemistry*, 1970, p. 1626.
Ley et al., *Tetrahedron Letters*, 1987, p. 225.
Ley et al., *Tetrahedron Letters*, 1988, p. 5305.
Hudlicky et al., *J. Org. Chem.*, 1989, p. 4239.
Hudlicky et al., *J. Am. Chem. Soc.*, 1988, p. 4735.

*Primary Examiner*—Ronald W. Griffin
*Attorney, Agent, or Firm*—Margaret A. Horn

[57] ABSTRACT

There are disclosed processes for the synthesis of substituted and unsubstituted arene diols useful in the further synthesis of sugars, sugar derivatives, chiral synthons or amino acids.

29 Claims, 3 Drawing Sheets

SYNTHESIS OF SUGARS FROM SUBSTITUTED AND UNSUBSTITUTED ARENE DIOLS

This application is a continuation-in-part of application Ser. No. 07/480,891 filed Feb. 16, 1990, now abandoned. This application is related to U.S. Ser. No. 07/636,396 filed Dec. 31, 1990, now abandoned.

The present invention relates to the synthesis of sugars and other chiral synthons from substituted and unsubstituted arene diols. Particularly, the present invention relates to synthesis of tetrose, pentose and hexose sugars which are useful for synthesis of other sugars and sugar derivatives.

BACKGROUND OF THE INVENTION

In 1970 Gibson and co-workers reported the enantioselective oxidation of toluene to cis-toluenediol [(+)-cis-2,3-dihydroxylmethylcyclohexa-4,6-diene] by a mutant of *Pseudomonas putida*, a soil bacterium [Gibson et al., J. Biochemistry 9:1626 (1970)]. Since that time many other simple arenes were shown to yield diols of this type through microbial oxidation techniques [Jerina et al., Arch. Biochem. Biophys. 142:394 (1971); Gibson et al., Biochemistry 7:3795 (1968); Jeffrey et al., Biochemistry 14:575 (1975); Burlingame et al., J. Bacteriol. 168:55 (1986); Gibson et al., Biochem. Biophys. Res. Commun. 50:211 (1973); Gibson et al., J. Bacteriol. 119:930 (1974); Whited et al., J. Bacteriol. 166:1028 (1986); Ziffer et al., Tetrahedron 33:2491 (1977)].

Despite the operational simplicity and complete stereospecificity of the reaction producing such diols, little use of this transformation has been made in organic synthesis, except for a few recent reports. [See for example: Hudlicky et al., J. Am. Chem. Soc. 110:4735 (1988) (used the toluene diol to synthesize enones useful for prostaglandin synthesis, aldehydes which are potential synthons for perhydroazulene terpenes, and cyclohexene oxide which is the descarbobenzoxy derivative of crotepoxide); Hudlicky et al., J. Org. Chem. 54:4239 (1989) (used the styrene diol to synthesize zeylena, cyclohexene oxide); Ley et al., Tetrahedron Letters 28:225 (1987) and Tetrahedron Letters 29:5305 (1988) (used the benzene diol to synthesize (+)-pinitol and inositol-1,4,5-triphosphate, respectively); and Johnson and Penning, J. Am. Chem. Soc. 108:4735 (1986) (reported a four step enantioselective synthesis of a prostaglandin intermediate in the shortest route to PGE2a, which was obtained by combination of the microbially derived chiral pool reagents with Johnson's procedure for the attachment of prostaglandin side chains)]. However, the full potential of such diols for synthesis of chiral synthons has not yet been fully realized.

At present, most commercially produced sugars (such as tetroses, pentoses, hexoses, polysaccharides, and derivatives thereof) are derived from natural sources or are produced by arduous chemical synthesis from other sugars. L-sugars have been particularly difficult to obtain by presently available synthetic means. The currently available processes for production of sugars and their derivatives have proven relatively inefficient and expensive. Thus, there is a need for a simple, efficient and cost effective method for synthesizing sugars and derivatives thereof, as well as for making other chiral synthons from readily available materials which can be transformed into the appropriate diols.

Currently, the well-accepted chiron approach to synthesis has relied on sugars, amino acids, or terpenoids as sources of chirality, but the crossover from one enantiomeric series to another almost always requires some redesign of the synthesis and the regeneration of the appropriate enantiomer of the starting material. [See for example: (a) Hanessian, S. *Total Synthesis of Natural Products: The Chiron Approach*. Baldwin, J. E., Ed.; Organic Chemistry Series, Vol. 3; Pergamon: Oxford, 1983. (b) MacGarvey, G. J., Williams, J. M. J. Am. Chem. Soc. 1985, 107, 1435; (c) Hanessian, S. Aldrichimica Acta, 1989, 22, 3.] Alternatively, the carbohydrate manifold has been reached from acyclic precursors in the approaches of Danishefsky [Bimwala, M.; de Guchteneere, E.; Vieira, E.; Wagner, J. *Trends in Synthetic Carbohydrate Chemistry*, Horton, D., Hawkins, L. D., McGarvey, G. J., eds., ACS Symposium Series, 1989, 386, 197] and Schmidt [Schmidt, R. R. *Trends in Synthetic Carbohydrate Chemistry*, Horton, D., Hawkins, L. D., McGarvey, G. J., eds., ACS Symposium Series, 1989, 386, 183] or from cyclic compounds in the approaches of Vogel [Vogel, P.; Auberson, Y.; Bimwala, M.; de Guchteneere, E.; Vieira, E.; Wagner, J. *Trends in Synthetic Carbohydrate Chemistry*, Horton, D., Hawkins, L. D., McGarvey, G. J., eds., ACS Symposium Series, 1989, 386, 197].

SUMMARY OF THE INVENTION

Such needs can be obviated by recognizing in accordance with the present invention, the relationship between arene diols and sugars and by taking advantage of the topological inversion of enantiomers through manipulations of the order of chemical events as shown in the simple example of generating synthons 17 and 18 from a single enantiomer 1 derived from chlorobenzene diol A as shown in FIG. 1. Either of the two enantiomers 17 or 18 is generated from a single enantiomer 1 derived by oxidative degradation of chlorobenzene via cis-diol 1. By varying the order and the type of chemical operations at each of the localities (a) and (b) in 1, a net enantiomeric transposition takes place. Therefore, through the degree of oxidation at (a) and (b), synthon 1 represents a chiral equivalent of meso-tartaric acid, which itself could not have any application in enantioselective synthesis, whereas the chiral equivalent, synthon 1 plays an important role in enantioselective synthesis.

As shown in the Figures, in accordance with the present invention, arene diols are amenable to conversion to various complex carbohydrates by simple oxidative manipulations. The most important feature of such conversions is the enantiodivergency of the approach. As shown in FIG. 1, the crossover is possible by selection of the order and the type of transformations of the initially formed lactones of type 1. By the one-carbon loss and two-carbon loss oxidative pathways, more complex sugars can be produced as well. The type of sugar or its diastereomeric configuration can be addressed by well established procedures for chain extension or contraction and by manipulations of specific centers in existing carbohydrates. [See for example: (a) Hanessian, S. *Total Synthesis of Natural Products: The Chiron Approach*. Baldwin, J. E., Ed.; Organic Chemistry Series, Vol. 3; Pergamon: Oxford, 1983. (b) MacGarvey, G. J., Williams, J. M. J. Am. Chem. Soc. 1985, 107, 1435; (c) Hanessian, S. Aldrichimica Acta, 1989, 22, 3 and (d) Garner, P. *Studies in Natural Products Chemistry*, Atta-ur-Rahman, ed., 1988, 1A, 397 (Elsevier); (e) Crimmins, M. T.; Hollis, W. G., Jr.; O'Mahony, R. *Studies in Natural Products Chemistry*, Atta-ur-Rahman, ed., 1988, 1A, 435 (Elsevier)].

The present invention provides methods for synthesizing sugars from arene diols which may be obtained as products of microbial oxidation reactions. Such methods are relatively simple and more economical than prior methods for such syntheses. A further advantage is provided by such methods in that sugars can be produced from arenes (such as chlorobenzene, polychlorobenzene, styrene, etc.) which are usually considered to be inexpensive, sometimes toxic, waste products. Thus, such waste or by-products can be converted into useful sugars in accordance with the present invention. The methods disclosed herein also allow simpler schemes for synthesis of L-sugars and provide opportunities at each reaction step where isotopically labelled sugars can be produced by using isotopically labelled reagents. It is understood that amino acids could also be synthesized from the resultant sugars in accordance with known methods, and as such, the invention described herein should not be limited by the nature of the end-product made by these novel pathways. These and other advantages of the present invention will be apparent to those skilled in the art from the disclosure herein.

DETAILED DISCUSSION

The present invention relates to the recognition that arene cis-diols, especially those derived from halobenzenes, reflect the latent oxidation state and stereogenic constitution of carbohydrates, which can therefore be manufactured from such arene cis-diols. Thus the enzymatic dioxygenation can be viewed as providing a chiral substance that resembles a generalized carbohydrate backbone from which several oxygen functionalities have been removed. The methods of the present invention, as further described below, provide methods for the chemical synthesis of sugars and sugar derivatives from these diols. Further described are novel intermediate compounds derived by the processes of the present invention.

Generally, in accordance with the methods of the present invention, 6-, 5- and 4-carbon sugars are synthesized from the appropriate diol by various permutations and combinations of reactions including, but not limited to, epoxidation, hydroxylation, reduction, carbon center inversion, olefination and cyclization reactions. These reactions add and remove carbon atoms from a given carbon moiety, create chiral carbon centers, provide functionalities (such as hydroxyl, keto, aldehyde, alcohol, acid groups, etc.), change the oxidation state of carbon centers, change the stereometric orientation around carbon centers and form cyclic moieties. Such reactions are individually known in the art, but are described herein for the first time in combination, to produce sugars, sugar derivatives and/or useful chiral synthons from arene diols, which should be considered unusual starting materials for sugar synthesis.

The order in which these various reactions are employed depends upon the product intended as the end result of the synthesis. For different sugars, certain steps may be repeated or may be performed in an order different from that for other sugars. However, examination of the chemical constituents of a desired sugar readily reveals the operations necessary for synthesizing such sugar from a given arene diol as is taught in the examples herein. And it is expected that one skilled in the art could make various end products not specifically exemplified herein, using the methods and novel intermediate compounds described herein.

Figure 1:
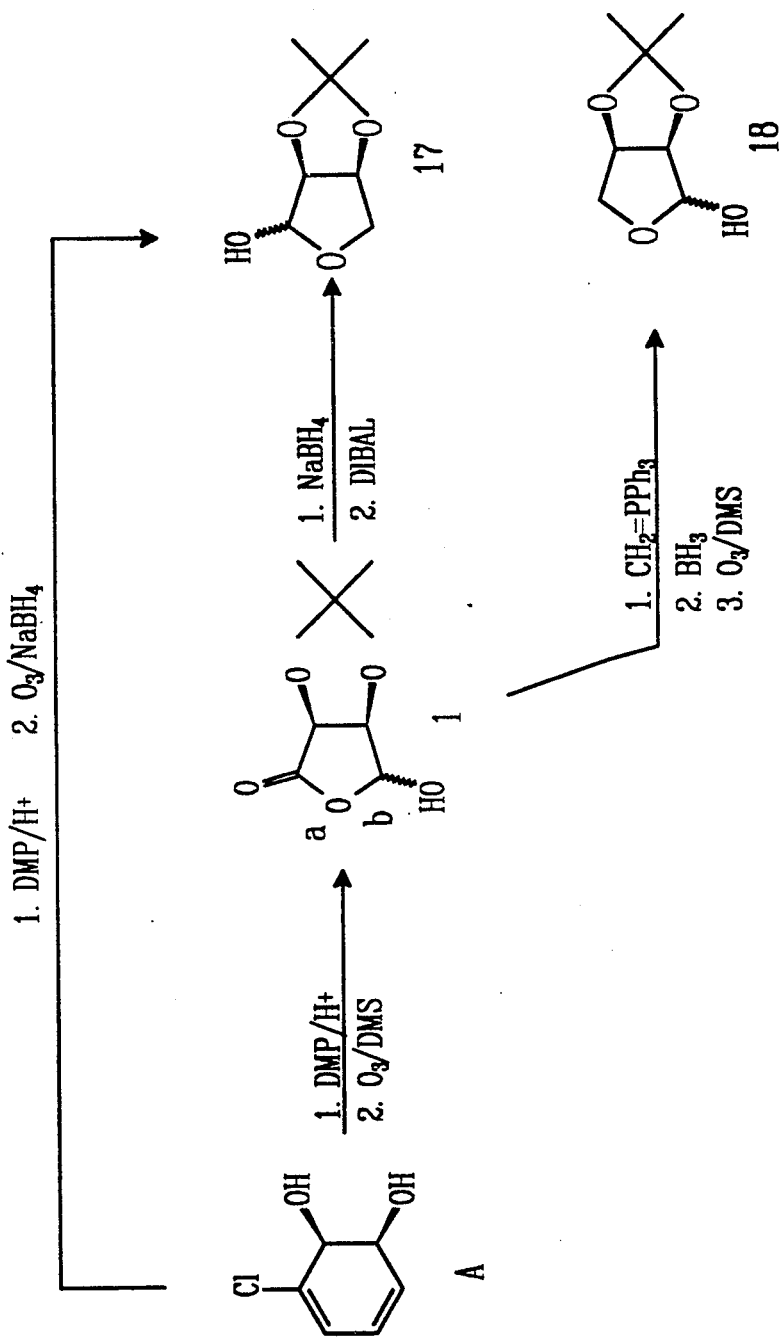
FIG. 1 is a generalized scheme for synthesis of a tetrose from an arene diol.

For example, L- and D-erythrose derivatives 17 and 18 were obtained from 1 by modifying the order of chemical events described above. Reduction of 1 with $NaBH_4$ gave 17 whereas an olefination, reduction and ozonolysis sequence yielded 18. The key to this divergent strategy is the initial backbone of a latent sugar, such as 1 or A (see FIG. 1) and the recognition that the presence of a halide atom allows distinction between pro-D and pro-L spaces of this molecule.

Figure 3:
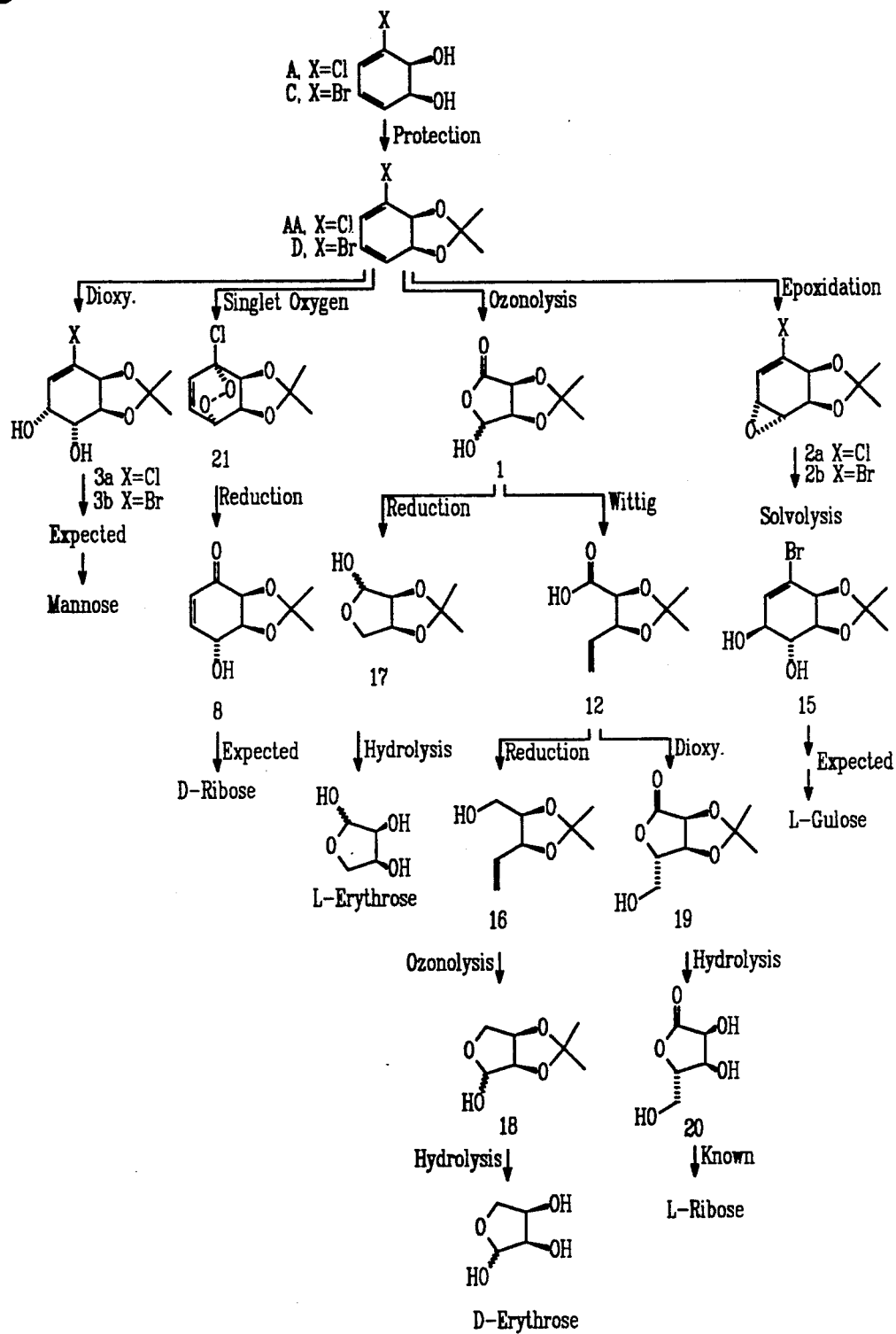
FIG. 3 is a generalized scheme encompassing the completed synthesis of a given example herein.

Hexoses are synthesized from a 6-carbon backbone moiety derived from the 6 carbon arene moiety. Pentoses and tetroses are synthesized from 5- and 4-carbon backbone moieties formed by removing carbon from the 6-carbon arene moiety. Depending upon (a) the substitution, if any, of the arene diol used in a given synthesis, and (b) the type and order of reaction steps used in the conversion of the diol to a sugar, the relevant 6-, 5- or 4-carbon backbone moiety is altered during the various reaction steps to change its functionalities as necessary to produce the desired sugar. In some instances, for example the synthesis of D-erythrose disclosed herein, additional carbons may be added to and removed from the relevant backbone moiety during synthesis. However, for the purpose of the appended claims, reaction and/or manipulation of backbone moieties to which additional carbons have been added is still considered a manipulation of the relevant backbone moiety derived from the arene moiety. For example, the conversion of acid 12 to alcohol 16 as shown in FIG. 3 is a reaction involving the 4-carbon backbone moiety originally derived from the diol A upon the conversion of acetonide AA to hydroxylactone 1 by ozonolysis.

Figure 2:
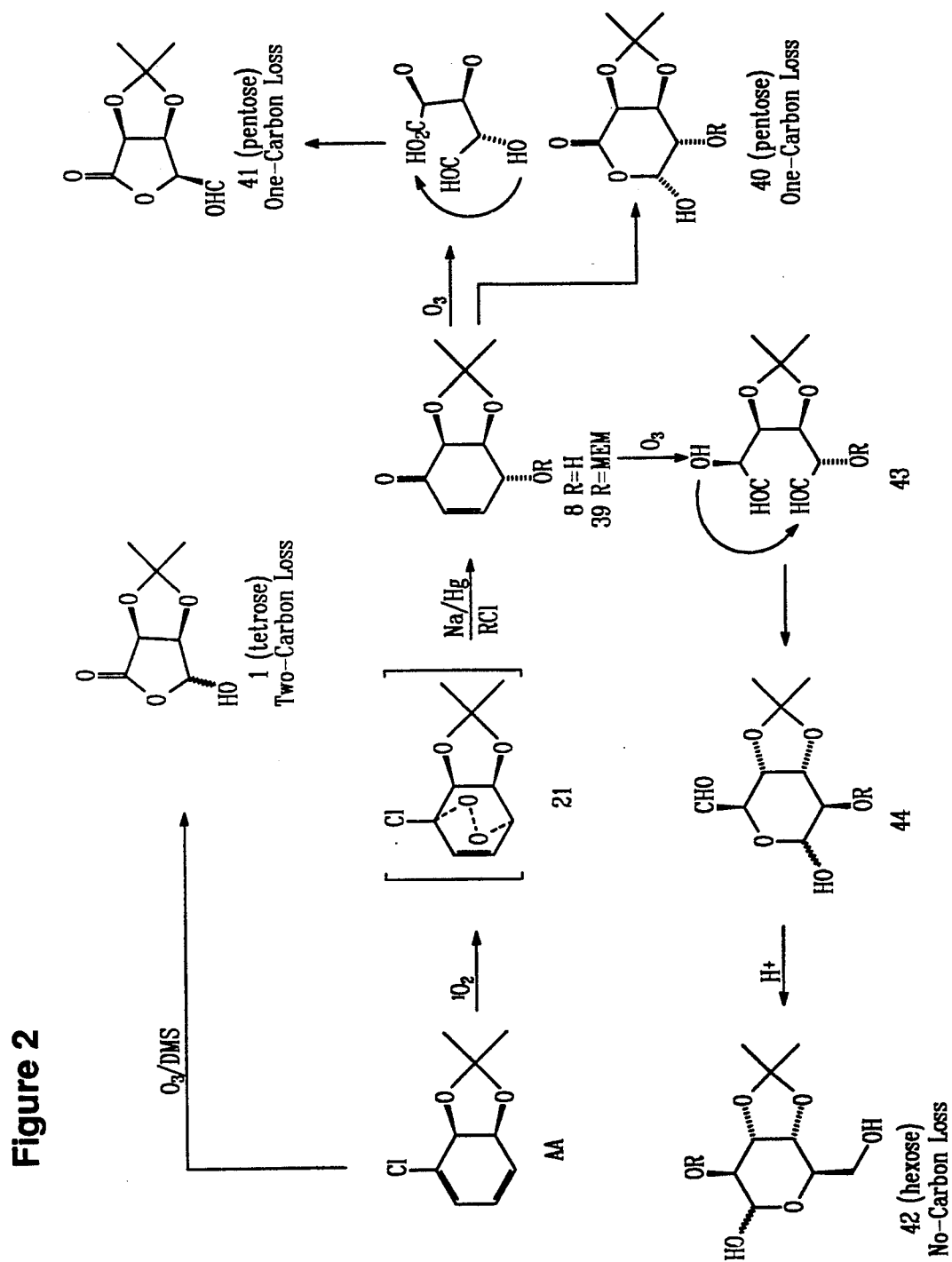
FIG. 2 is a generalized scheme for synthesis of sugars from arene diols.

In accordance with the present invention, a method for preparation of carbohydrates is disclosed which recognizes that acetonide AA is a latent synthon for tetroses, pentoses, and hexoses through further, properly controlled, oxidation. For example, as shown in FIG. 2, an oxidation with a net loss of two carbons leads to the above tetrose synthon 1. This two step process (going from AA to 1) is an improvement over the systems known in the art such as described by Bergman, R. et al, J. Chem. Soc. Commun., 865 (1990) and Beer, O. et al, Helvetica Chimica ACTA, 65: 2570 (1982). A one-carbon loss from the enone 8 generated from the endoperoxide 21 is expected to lead to a pentose derivative 40 and 41, while reduction of 8 followed by ozonolysis with no carbon loss should give 43, which may be converted via 44 to the rare sugar D-altrose 42. Once compounds such as 17, 40, 41 and/or 42 have been made by methods described in the present application, other diastereomeric sugar derivatives can be reached from such compounds by application of existing manipulations aimed at the inversion of selected centers as delineated by Hanessian in the chiron-based approach to the synthesis of complex molecules from carbohydrates [see for example, (a) Hanesian, S. *Total Synthesis of Natural Products: The Chiron Approach.* Baldwin, J. E., Ed.; Organic Chemistry Series, Vol. 3; Pergamon: Oxford, 1983. (b) MacGarvey, G. J., Williams, J. M. J. Am. Chem. Soc. 1985, 107, 1435; (c) Hanessian, S. Aldrichimica Acta, 1989, 22, 3; (c) Garner, P. Studies in Natural Products Chemistry, Atta-ur-Rahman, ed., 1988, 1A, 397 (Elsevier); (d) Crimmins, M., T.; Hollis, W. G., Jr.; O'Mahony, R. Studies in Natural Products Chemistry, Atta-ur-Rahman, ed., 1988, 1A, 435 (Elsevier)].

Hexoses can be synthesized from arene diols, for example, as shown in FIG. 2. Appropriate permutations and combinations of reactions to produce the desired functionality in the hexose is dictated by the desired end product.

Pentoses can be synthesized from arene diols by first removing one carbon from the diol (e.g., by the addition of singlet oxygen across the arene moiety (with subsequent degradation by ozonolysis)). The 5-carbon product is then converted into the desired sugar, for example, as shown in FIG. 2. Other examples of pentose synthesis are illustrated in FIG. 3. Appropriate permutations and combinations of reactions to produce the desired functionality in the pentose is dictated by the end product desired.

Similarly, tetroses can be synthesized from arene diols by first removing two carbons from the diol (e.g., by ozonolysis) as shown in FIG. 2. The 4-carbon product is then converted into the desired sugar. Tetrose synthesis is exemplified by the synthesis of L and D-erythrose as shown in FIG. 3. Chlorobenzene was oxidized using a process modified from that for preparation of the toluene diol [Hudlicky et al., J. Am. Chem. Soc. 110:4735 (1988)]. The diol A was protected as its acetonide AA and ozonized to the hydroxylactone 1. [See Ballou, J. Am. Chem. Soc. 79:165 (1957)].

Pentoses and hexoses can also be formed through a five- or six-carbon hydroxylactone intermediate made by alkylation of hydroxylactone 1, for example as shown in FIG. 3. The new hydroxylactone so formed can then be processed as described to provide additional functionality.

Substituted sugars and sugar derivatives can be synthesized in accordance with the present invention from appropriately substituted arene diols. Arene diols of the general formula (I):

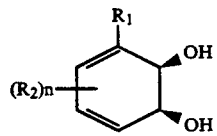

can be used in the methods of the present invention, wherein R1, R2, R3, R4, R5 and R6 can be any substituent. Preferably, R1 is halogen, lower alkyl (C1–C6), lower alkenyl (C1–C6) or lower alkynyl (C1–C6) and R2 is hydrogen, halogen or lower alkyl (C1–C6). Since the arene diols are synthesized by microbial oxidation, substitution of the arene diol is limited only by the microbial process (i.e., by the substituted arenes which can serve as a substrate for the microbial process).

Examples in the present invention use chloro and bromobenzene diols (R1=Cl or Br), however, it is understood that other substituents, for example R1=CN, OR, CO2R, may be tolerated in the described processes. The use of benzene diol (R1=H) has been reported by Ley and Carless. Carless et al, Tetrahedron Letters 30:3113, 1989; Carless et al, Tetrahedron Letters 30:1719, 1989; Ley et al, Tetrahedron Letters 45:3463, 1989; Ley et al, Tetrahedron Letters 29:5305, 1988. However, the incorporation of benzenediol to asynthesis such as those described herein requires additional steps to define asymmetry (resolution). Consequently, it is much more convenient and efficient to use halobenzenes and their diols in the processes described herein. Halogen is an ideal functionality since it defines asymmetry in the molecule and it can be easily removed. The processes described herein disclose the first use of diols derived from halobenzenes in the synthetic design of chiral products.

Sugars produced in accordance with the present invention can also be used according to known methods in the synthesis of other sugars and sugar derivatives. Sugars produced according to the present invention can also be recyclized by known methods to produce other derivatives. For example, various pentoses can be recyclized to form the corresponding erythronolactones, which are useful as termini for antibacterial and antiviral agents. It is understood that various amino acids could also be synthesized from sugars produced in accordance with the present invention. Methods for synthesis of amino acids from appropriate sugars are well known in the art (for example, those disclosed in Specialist Periodical Reports, Chem. Soc. London, Vol. 1–14).

The synthesis of both enantiomers of erythrose from a single intermediate 1 as exemplified herein underscores the potential benefits of the enantiodivergent methodology described for the first time herein. Both enantiomers of ribonolactone may be obtained from 12 (L) and 21 (D) respectively, the latter compound is expected to be converted to D-ribose.

Potential conversion of 2a and 3a (FIG. 3) to diastereomeric hexoses is expected. These synthons (2a and 3a) contain a more diversified sugar backbone which through the application of olefin cleavage (ozonolysis) and reduction with concomitant cyclization result in the hexose structure.

Key synthetic intermediates which have been made via the present invention which may be useful in the synthesis of chiral compounds including, but not limited to, sugars, sugar derivatives, amino acids or chiral synthons, are outlined in FIG. 3. The detail of these syntheses and their structure determinations are described as follows.

(2S,3S)-2,3-O-Isopropylidene-1-chlorocyclohexa-4,6-diene AA

To a solution of dienediol A (736.5 mg, 4.646 mmol), in 10 mL of 2,2-dimethoxypropane (DMP)-acetone (3:1) was added a catalytic amount of p-toluensulfonic acid, and the reaction mixture was stirred at room temperature, protected from moisture, for 30 min. The dienediol A was obtained as described by Gibson, D. T.; Hensley, M.; Yoshika, H.; Mabry, R. J. Biochemistry 1970,9,1626. To the mixture was added 5 mL of 10% aqueous NaOH, and the reaction mixture was stirred for 10 min. The reaction mixture was diluted with 10 mL of ethyl acetate, and the organic layer was washed with brine (3×5 mL). The organic extracts were dried over sodium sulfate, and the solvent was evaporated, yielding 832 mg (95%) of a colorless liquid: $R_f=0.8$ (hexane-ethyl acetate, 8:2); $[\alpha]^{25}_D = +45°$ (c 0.50, CHCl3); IR (neat) 2988, 2935, 2898, 1652, 1380 cm$^{-1}$; $^1$H NMR (CDCl3) δ 6.05 (d, J=5.5 Hz, 1H), 5.85 (m, 2H), 4.7 (dd, J=3.4 Hz, J=8.8 Hz, 1H) 4.57 (d, J=8.8 Hz, 1H), 1.36 (s, 6H); $^{13}$C NMR (CDCl3) δ 133.3, 124.0, 123.2, 121.6, 106.3, 74.7, 72.6, 26.6, 24.9.

2,3-O-Isopropylidene-D-erythruronolactone 1

A solution of diene AA, made by the process described above (94 mg, 0.5 mmol) in 7 mL of ethyl acetate was cooled to −78° C., and a stream of $O_2/O_3$ was passed through until the persistence of a blue color. Nitrogen was bubbled through the solution to remove the excess ozone. Dimethyl sulfide (DMS, 1.4 mL) was added, and the temperature was immediately raised to 0° C. The reaction was stirred for 12 h and then diluted with 30 mL of ether. The ethereal solution was washed with water (1×5 mL) and brine (1×5 mL). The solution was dried ($Na_2SO_4$) and filtered, and the solvent was evaporated, yielding 70.7 mg of crude product (80%). After purification (chromatography, 10% deactivated silica gel, methylene chloride/acetone, 7:3), 30.4 mg of clean product was obtained (34.4%): $R_f$=0.2 (silica gel; chloroform/methanol, 8:2); $[\alpha]^{25}_D$= −60° (c 1.0, $CHCl_3$); IR (KBr) 3400, 1723 $cm^{-1}$; $^1H$ NMR ($CDCl_3$) δ 5.81 (s, 1H), 4.91 (m, 1H), 4.60 (d, 1H, J=5.4 Hz), 1.47 (s, 3H), 1.40 (s, 3H); $^{13}C$ NMR ($CDCl_3$) δ 174, 114, 99, 95, 80, 74, 27, 26 ppm. Spectral data were in agreement with literature values. [See: Beer, D.; Meuwly, R.; Vasella, A. Helv. Chim. Acta 1982, 65, 2571.]

2,3-O-Isopropylidene-L-erythrose 17

Method A

A solution of 78.4 mg (0.5 mmol) of diene AA (made by the process described above) in 7 mL of methanol-methylene chloride (8:2) was cooled to −78° C., and a stream of $O_3/O_2$ was passed through until the persistence of a blue color. Nitrogen was bubbled through the solution to remove excess ozone. To the stirred reaction, at −78° C. under nitrogen atmosphere, was added 36 mg (0.5 mmol) of $NaBH_4$, stirring was continued for 1 h, the temperature was raised to 0° C., and the solution was stirred for an additional hour. After that, 10 drops of a saturated aqueous solution of $NH_4Cl$ was added, and the solvent was removed under reduced pressure, without heating. The semisolid residue was taken up in ethyl acetate (5 mL) and filtered; this operation was repeated twice. The combined organic extracts were evaporated to produce 74 mg of a colorless viscous liquid. Separation by preparative TLC (silica gel; hexanes-ethyl acetate, 6:4) produced the following.

2,3-O-Isopropylidene-4-O-methyl-L-erythruronolactone (11.6 mg, 12%): $R_f$=0.55 (silica gel; ethyl acetate-hexane, 1:1); mp 76°–78° C.; $[\alpha]^{25}_D$= −66.35° (c 4.75, MeOH); IR (neat) 2985, 2920, 1710 $cm^{-1}$; $^1H$ NMR ($CDCl_3$) δ 5.34 (s, 1H), 4.8 (d, J=5.5 Hz, 1H), 4.55 (d, J=5.5 Hz, 1H), 3.53 (s, 3H), 1.46 (s, 3H), 1.38 (s, 3H); $^{13}C$ NMR ($CDCl_3$) δ 114 (C), 105 (C), 79 (CH), 74 (CH), 60 (CH), 26 (CH), 25 (CH); MS (Cl) calcd for $C_8H_{12}O_5$ 188.07629, found 188.07574. 2,3-O-Isopropylidene-L-erythrose 17 (41.6 mg, 52%): $R_f$=0.34; $^1H$ NMR ($CDCl_3$) δ 5.4 (d, 1H), 4.85 (m, 1H), 4.59 (d, 1H), 4.05 (m, 2H), 1.48 (s, 3H), 1.32 (s, 3H); spectral data were in agreement with literature values $[\alpha]^{25}_D$= +75° (c 1.0, $CH_3OH$). [See: Ballou, C. E. J. Am. Chem. Soc. 1957, 79, 165.]

Method B

To a solution of L-erythruronolactone 1 (17.4 mg, 0.10 mmol) in methanol (2 mL) was added 5 mg (0.13 mmol) of $NaBH_4$. The mixture was stirred at room temperature for 15 minutes and diluted with a further 4 mL of methanol, and MeI was added (0.5 mL). This solution was heated to reflux for 8 h and evaporated to dryness, and the residue was extracted with $CHCl_3$ (3×10 mL). After evaporation, purification by chromatography (silica gel; EtOAc-hexane, 1/1) afforded 9.1 mg (0.075 mmol, 75%) of 2,3-O-isopropylidene-L-erythrolactone 50: $R_f$=0.50 (hexane-EtOAc, 1:1); mp 64° C. $[\alpha]^{25}_D$= +106° (c 0.91, acetone). Spectral data were in agreement with literature values: $[\alpha]^{25}_D$= +105° (c 1.0, $H_2O$)[see: Lager, W.; Hafele, B. Synthesis 1987, 803]. To a solution of lactone 50 (9.1 mg, 0.057 mmol) in 4 mL of $CH_2Cl_2$ at −78° C. was added 0.08 mL of a 1M hexane solution of DIBAL. The reaction was stirred for 4 h and quenched by the addition of MeOH and $H_2O$. The solution was diluted with EtOAc (5 mL), and the pH was carefully adjusted to 3 by the addition of dilute sulfuric acid. The organic fraction was concentrated, leaving a yellow oil which after chromatography (silica gel; EtOAc-hexane, 6:4) afforded 7.5 mg (0.047 mmol, 82%) of 2,3-isopropylidene-L-erythrose 17, identical with material obtained by method A above.

(2S,3S)-2,3-O-Isopropylidene-4-pentenoic Acid 12

To a solution of triphenylmethylphosphonium bromide (1.07 g, 3.0 mmol) in THF was added 3.1 mmol of n-BuLi (1.2 mL, 2.5M in hexane) at 0° C. After warming to 25° C., 174 mg (1.0 mmol) of hydroxy lactone 1 in 5 mL of THF was added. The solution was heated to reflux for 1 h and then stirred at 25° C. for 8H. The reaction mixture was poured into $H_2O$ (30 mL). The aqueous layer was washed with ether (3×15 mL), acidified with acidic resin (Amberlite IR-120), and extracted with $CH_2Cl_2$ (3×30 mL.) The $CH_2Cl_2$ fractions were combined, dried ($Na_2SO_4$), and concentrated. Purification by Kugelrohr distillation (90°–100° C., 0.005 mm) afforded 103 mg (60%) of the vinyl acid 12 as a colorless oil: $[\alpha]^{25}_D$= +22.8° (c 2.60, $CHCl_3$). Spectral data were in agreement with literature values: $[\alpha]^{20}_D$= +24° (c 1.56, $CHCl_3$). [See: Lager, W.; Hafele, B. Synthesis 1987, 803.]

(2R,3S)-2,3-O-Isopropylidene-4-pentenol 16

To a solution of 52 mg (0.30 mmol) of pentenoic acid 12 in ether (10 mL) was added 45 mg (1.2 mmol) of LAH at 0° C. The mixture was warmed to room temperature and stirred for 3 h. The reaction was quenched by the addition of $H_2O$ (45 μL) and 15% aqueous NaOH (150 μL), and the solution was filtered through a short column of silica gel. Concentration afforded 45 mg (95%) of pure alcohol 13: $[\alpha]^{25}_D$= +41.0° (c 2.25, $CHCl_3$); $R_f$=0.50 (hexane-EtOAc, 1:1) Spectral data were in agreement with literature values: $[\alpha]^{20}_D$= +44° (c 4.89, $CHCl_3$). [See: Lager et al., supra.]

2,3-O-Isopropylidene-D-erythrose 18

Pentenol 16 (158 mg, 1.00 mmol) was dissolved in $CH_2Cl_2$ (10 mL), and ozone was bubbled through the solution at −78° C. until persistence of a blue color. Excess ozone was removed by a stream of $N_2$. Dimethyl sulfide (0.2 mL) was added, and the solution was stirred for 4 h at room temperature. The reaction mixture was washed with $H_2O$ (5×5 mL), dried ($Na_2SO_4$), and concentrated. Purification by flash chromatography (silica gel; EtOAc-hexane, 6:4) afforded 88 mg (0.55 mmol, 55%) of lactol 18: $[\alpha]^{25}_D$= −71° (c 3.02, $CHCl_3$); $R_f$=0.50. Spectral data were in agreement with literature values: $[\alpha]^{25}_D$= −77.0° (c 2.09, $CHCl_3$). [See: Hudlicky, T.; Seoane, G.; Lovelace, T. C. J. Org. Chem. 1988, 53, 2094.] Additionally, this material proved identical to a sample prepared from D-arabinose [Ballou, C. E. supra].

L-Ribonolactone 19

Olefinic acid 12 (12 mg), OSO$_4$ (2 drops) acetone (0.5 mL), and H$_2$O (100 mL) were mixed and stirred at rt overnight. The mixture was purified by a short silica column to give 4 mg of 19, identical to material obtained by conversion of commercial L-ribonolactone to its acetinide [$\alpha_D$=+52° and NMR].

(1R,4S,5R,6S)-1-Chloro-7,8-dioxa-5,6-di-O-isopropylidenebicyclo[2.2.2]oct-2-ene 21

Tetraphenylporphine (Tpp) (3 mg) was dissolved in chloroform (5 mL), 10 minutes before initiation of the reaction; this solution was transferred to the reaction vessel (a water jacketed flask, with 2 necks and a glass frit bubbler attached) using CCl$_4$ (50 mL). The acetonide AA (736 mg, 4.65 mmoL) was added to the reaction vessel using CCl$_4$ (50 mL). The temperature of the reaction mixture was kept ~20° C. while oxygen was bubbled through the solution irradiated with a quartz lamp (500 W). The reaction was monitored by TLC (hexane/ethyl acetate, 9:1) and it was complete in 2.5 h. The solvent was removed under reduced pressure without heating. The dark green residue was taken up in hexane (80 mL) and shaken for 5 min with charcoal (0.5 g); the mixture was filtered through Celite ®. Evaporation of the solvent afforded 950.9 mg (4.32 mmol, 93%) of clean endoperoxide as light brown crystals, which could be used without further purification (mp=69°–71° C.). An analytical sample was obtained by sublimation (<30° C., 0.005 torr) mp=74°–76° C.; R$_f$=0.5 (chloroform); [$\alpha$]$^{25}_D$=+57.42° (c 0.5, MeOH); FTIR (KBr) 2994, 2936, 1381 cm$^{-1}$; $^1$H NMR (CDCl$_3$) δ 6.60 (ddd, J=8.7, 5.0, 0.9 Hz, 1H), 6.50 (ddd, J=8.7, 1.4, 1.2 Hz, 1H), 4.95 (ddd, J=7.0, 4.4, 0.9 Hz, 1H), 4.73 (ddd, J=5.0, 4.4, 1.4 Hz, 1H), 4.5 (dd, J=7.0, 1.2 Hz, 1H), 1.37 (s, 3H), 1.34 (s, 3H); $^{13}$C NMR (CDCl$_3$) δ 133.7, 131.7, 111.3, 95.0, 78.8, 74.1, 73.1, 25.6, 25.4.

(4R,5S,6R)-4-Hydroxy-5,6-di-O-isopropylidenecyclohex-2-en-1-one 8

To a solution of endoperoxide 21 (951 mg, 4.36 mmol) in MeOH (6 mL) at 10° C. was added thiourea (364 mg, 4.79 mmol) in MeOH (5 mL) dropwise. After the addition was complete the reaction mixture was stirred at room temperature (rt) for 0.5 h; the solvent was evaporated under reduced pressure at rt. The residue was quickly diluted with ethyl ether (50 mL), and filtered through Celite ®. The filtrate was evaporated to produce a viscous yellow oil. The crude product was purified by flash chromatography (silica gel, methylene chloride-acetone, 8:2) to afford 680 mg (3.71 mmol, 85%) of a light yellow oil, which slowly solidified: mp=72°–72.5° C.; R$_f$=0.21 (ethyl acetate/hexane, 1:1); [$\alpha$]$^{25}_D$=−53.4° (c 0.0105, MeOH); FTIR (neat) 3444, 2989, 2937, 1682, 1378 cm$^{-1}$; $^1$H NMR (CDCl$_3$) δ 6.87 (dd, J=10.3, 3.2 Hz, 1H); 6.11 (dd, J=10.3, 1.6 Hz, 1H), 4.58 (br s, 1H), 4.46 (m, 2H), 4.18 (br s, 1H), 1.4 (s, 6H); $^{13}$C NMR (CDCl$_3$) δ 195.1, 148.3, 127.9, 110.1, 79.0, 74.0, 65.9, 27.1, 25.6; mass spectrum (EI, 70 eV) m/e (rel intensity) 184 (M+, 0.06), 169 (0.26), 155 (0.20), 126 (0.18), 97 (1.00); Anal. calcd for C$_9$H$_{12}$O$_4$: C, 57.68; H, 6.57. Found: C, 58.15; H, 6.56.

(1R,4S,5S,6R)-3-Chloro-4,5-di-O-isopropylidene-7-oxabicyclo[4.1.0]hept-2-ene 2a To a solution of diene AA [Gibson et al., supra] (1.915 g, 10.3 mmol) in CH$_2$Cl$_2$ (75 mL) at 0° C. was added mCPBA (1.78 g, 8.2 mmol) portionwise. The solution was allowed to warm to room temperature and stirred for 8 h. The reaction mixture was washed with 15% aq sodium sulfite (2×50 mL), saturated aq sodium bicarbonate (2×50 mL), and water (50 mL), then dried (MgSO$_4$), filtered, and concentrated. Unreacted starting material was removed under vacuum leaving 1.50 g (7.3 mmol, 89%) of pure epoxide 2a as a colorless solid: mp=59°–60° C.; R$_f$=0.76 (hexane/EtOAc, 1:1); [$\alpha$]$^{25}_D$=+40.2° (c0.21, CHCl$_3$); FTIR (KBr) 2989, 2936, 1643, 1383, 1373 cm$^{-1}$; $^1$H NMR (CDCl$_3$) δ 6.19 (dd, J=4.4, 1.0 Hz, 1H), 4.84 (dt, J=6.8, 1.4 Hz, 1H), 4.34 (d, J=6.8 Hz, 1H), 3.55 (dd, J=3.5, 1.4 Hz, 1H), 3.36 (td, J=5.4, 4.4 Hz, 1H), 1.42 (s, 3H), 1.40 (s, 3H); $^{13}$C NMR (CDCl$_3$) δ 137.9, 122.2, 111.4, 73.1, 72.6, 49.6, 47.9, 27.4, 25.8; mass spectrum (Cl, 70 eV) m/e (rel intensity) 203 (M+, 0.22), 187 (0.13), 145 (1.00), 109 (0.46); HRMS calcd for C$_9$H$_{11}$ClO$_3$: 202.0485; Found: 202.0475.

(1R,4S,5S,6R)-3-Bromo-4,5-di-O-isopropylidene-7-oxabicyclo[4.1.0]hept-2-ene 2b To a solution of acetonide D, prepared by the method for synthesis of AA, (1.0 g, 4.33 mmol) in CH$_2$Cl$_2$ (40 mL) was added mCPBA (1.1 g, 5.19 mmol) in one portion. The reaction mixture was stirred at room temperature for 12 h. The mixture was filtered, the filtrate was treated with 10% aqueous sodium sulfite (5 mL) and separated. The organic layer was washed with H$_2$O (10 mL), 10% aq NaOH (10 mL) and brine (10 mL), dried (Na$_2$SO$_4$) and evaporated under reduced pressure. The crude product was purified by flash chromatography (silica gel, hexane/ethyl acetate, 4:1) to afford 871 mg of colorless crystals (3.55 mmol, 82%): mp 78°–78.5° C.; R$_f$=0.70 (hexanes/EtOAc, 4:1);[$\alpha$]$^{25}_D$=+103.8° (c0.53, MeOH); IR (KBr) 3923, 2990, 2936, 2890, 1633 cm$^{-1}$; $^1$H NMR (CDCl$_3$) δ 6.48 (dd, J=4.5, 1.2 Hz, 1H), 4.88 (ddd, J=6.8, 1.8, 1.0 Hz, 1H), 4.43 (dd, J=6.8, 1.0 Hz, 1H), 3.59 (dd, J=6.8, 1.8 Hz, 1H), 3.34 (td, J=1.0, 3.8 Hz, 1H), 1.47 (s, 3H), 1.44 (s, 3H); $^{13}$C NMR (CDCl$_3$) δ 129.9 (C), 126.5 (CH), 111.4 (C), 74.2 (CH), 72.7 (CH), 49.5 (CH), 48.3 (CH), 27.5 (CH$_3$), 26.0 (CH$_3$); mass spectrum (EI, 70 eV) m/e (rel intensity) 248 (M+, 0.48), 246 (0.48), 233 (0.67), 231 (0.67), 161 (0.74), 159 (0.74), 109 (1.00), 81 (0.74); Anal. calcd for C$_9$H$_{11}$BrO: C, 43.75; H, 4.49. Found: C, 43.71; H, 4.50.

(1S,2R,3S,4S)-5-Bromo-1,2-dihydroxy-3,4-di-O-isopropylidene cyclohex-5-ene 15

To an ice-cooled solution of (1R,4S,5S,6R)-3-Bromo-4,5-di-O-isopropylidene-7-oxa-bicyclo[4.1.0]hept-2-ene 2b (465.3 mg, 1.88 mmoL) in DMSO (5 mL) was added an aqueous solution of 10% KOH (5 mL). The mixture was refluxed for 6 h. The aqueous solution was extracted with EtOAc (6×6 mL). The combined organic layers were dried over Na$_2$SO$_4$, filtered, and evaporated to dryness. The diol was purified by FCC (10% H$_2$O silica gel; 7.5:2.5, EtOAc/Hexane) and 316 mg (63%, 1.19 mmoL) of diol was obtained. The diol was recrystallized from CH$_2$Cl$_2$/Hexane. R$_f$=0.38 (4:1, EA-H); mp=147.0° C.; [$\alpha$]$^{20}_D$=−10.7° (c0.35, MeOH); IR (KBr) 3506, 3395, 2984, 1647, 1083, 1067 cm$^{-1}$; $^1$H-NMR (CDCl$_3$) δ 6.24 (1H, d, J=2.5), 4.66 (1H, d, J=6.1), 4.18 (1H, dd, J=7.9, 6.3), 4.06 (1H, m), 3.74 (1H, t, J=7.6), 2.92 (2H, bs), 1.52 (3H, s), 1.40 (3H, s); $^{13}$C-NMR (CDCl$_3$) δ 133.8 (CH), 120.2 (C), 111.1 (C), 77.6 (CH), 77.0 (CH), 73.1 (CH), 70.9 (CH), 28.0 (CH$_3$), 26.0 (CH$_3$); MS (m/z, relative intensity, Cl) 265 (M.+, 6), 249 (14), 189 (100), 170 (50), 161 (20), 111 (70); Anal. Calcd for C$_9$H$_{13}$O$_4$Br: C, 40.78; H, 4.94. Found: C, 40.51; H, 4.83.

(1R,2R,3S,4S)-5-chloro-1,2-dihydroxy-3,4-di-O-isopropylidenecyclohex-5-ene 3a

To a solution of diene AA [Gibson et al., supra] (1.00 g, 5.38 mmol) in acetone-water (3:1, 65 mL) N-Methylmorpholine-N-Oxide (NMO) (670 mg, 5.70 mmol) was added and 2 mL of a 2.5% solution of OsO$_4$ in t-butanol. The mixture was stirred at rt for 24 h. The solution was concentrated under reduced pressure, and acidified with 1M HCl. Excess OsO$_4$ was reduced by addition of 15% NaHSO$_3$ (190 mL) and NaCl was added to give a saturated solution. The resulting solution was extracted with EtOAc (10×50 mL). The organic fraction was dried (MgSO$_4$), filtered, and concentrated. Purification by flash chromatography afforded 1.06 g (4.84 mmol, 90%) of pure diol 3a as an oil: R$_f$=0.25 (hexane/EtOAc, 1:1); [α]$^{25}_D$=−8.1° (c 0.455,CHCl$_3$); FTIR (neat) 3358, 2987, 2923, 1651, 1382, cm$^{-1}$; $^1$H NMR (CDCl$_3$) δ 5.91 (d, J=3.4 Hz, 1H), 4.57 (d, J=5.5 Hz, 1H), 4.43 (t, J=5.5 Hz, 1H), 4.4–4.3 (m, 1H), 4.10 (dd, J=4.7, 4.7 Hz, 1H), 2.60 (br s, 2H), 1.41 (s, 3H), 1.38 (s, 3H); $^{13}$C NMR (CDCl$_3$) δ 26.1, 27.6, 66.6, 69.6, 75.0, 76.2, 110.4, 126.9, 132.8; mass spectrum (Cl, 70 eV) m/e (rel intensity) 221 (M+1, 0.81), 205 (0.47), 203 (0.40), 189 (0.26), 85 (1.00); HRMS calcd for C$_9$H$_{13}$Cl-O$_4$:220.0581; Found: 220.0601.

(1R,2R,3S,4S)-5-Bromo-1,2-dihydroxy-3,4-di-O-isopropylidene cyclohex-5-ene 3b

To a solution of acetonide D (887 mg, 3.33 mmol) in acetone-H$_2$O (3:1, 58 mL) were added 630 mg (5.38 mmol) of NMO and 2 mL of a 2.5 wt % solution of OsO$_4$ in t-butanol. The solution was stirred at room temperature for 8 h. After concentration, the solution was adjusted to pH 8–9 and treated with sodium bisulfite. The aqueous phase was extracted with EtOAc (30×10 mL). Purification by flash chromatography (silica gel, EtOAc/hexane, 2:1) afforded 885 mg (3.32 mmol, 97%) of colorless crystals: mp=113°–114° C.; R$_f$=0.50 (hexanes/EtOAc, 1:2); [α]$^{25}_D$= −11.6° (c2.88, CHCl$_3$); FTIR (KBr) 3400, 2998, 2940, 2898, 1656 cm$^{-1}$; $^1$H NMR (CDCl$_3$) δ 6.13 (d, J=3.2 Hz, 1H), 4.62 (d, J=5.4 Hz, 1H), 4.41 (t, J=5.4 Hz, 1H), 4.30 (br s, 1H), 4.12 (br s, 1H), 3.5 (br s, 2H), 1.41 (s, 3H), 1.38 (s, 3H); $^{13}$C NMR (CDCl$_3$) δ 131.2 (CH), 123.7 (C), 110.3 (C), 76.4 (CH), 76.3 (CH), 69.5 (CH), 67.4 (CH), 27.7 (CH$_3$), 26.2 (CH$_3$); mass spectrum (EI, 70 eV) m/e (rel intensity) 266 (M+, 0.05), 264 (0.05), 251 (0.90), 249 (0.09), 110 (0.44), 101 (1.00); Anal. calcd for C$_9$H$_{13}$BrO$_4$: C, 40.76; H, 4.90. Found: C, 40.70; H, 4.90.

Each of the references cited herein is incorporated by reference as if fully set forth.

What is claimed:

1. A method for producing a diene useful as an intermediate agent, said method comprising:
  a. providing a substituted arene diol of the formula:

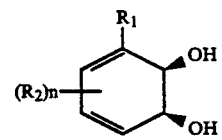

wherein:
    R$_1$ is halogen, lower alkyl, lower alkenyl, lower alkynyl, CN, OR, or CO$_2$R;
    R$_2$ is H, halogen, lower alkyl or a bridging group between two arene moieties;
    R is H or lower alkyl; and n is 0 to 5;
  b. protecting such diol as a chiral diol to allow for face selectivity in subsequent hydroxylation or oxygenation methods, said protected diol having the formula:

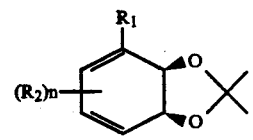

wherein R$_1$ and R$_2$ are as defined above.

2. A method of claim 1 wherein R$_1$ is Cl or Br.

3. A method of claim 1 wherein the arene diol is selected from the group consisting of: (+)-cis-2,3-dihydroxy-cyclohexa-4,6-diene; (+)-cis-2,3-dihydroxy-1-methyl-cyclohexa-4,6-diene; (+)-cis-2,3-dihydroxy-1-chloro-cyclohexa-4,6-diene; (+)-cis-2,3-dihydroxy-1-bromo-cyclohexa-4,6-diene; and (+)-cis-2,3-hydroxy-1-ethenyl-cyclohexa-4,6-diene.

4. A method of claim 3 wherein the arene diol is (+)-cis-2,3-dihydroxy-1-chloro-cyclohexa-4,6-diene.

5. A method of claim 3 wherein the arene diol is (+)-cis-2,3-dihydroxy-1-bromo-cyclohexa-4,6-diene.

6. A method for producing sugars, sugar derivatives, or other chiral synthons which comprises converting into such the dienes 17 or 18 of claim 1.

7. A method for producing 2,3-O-isopropylidene-L-erythrose 17 useful as an intermediate compound, said method comprising:
  a. treating (2S,3S)-2,3-O-isopropylidene-1-chlorocyclohexa-4,6-diene AA with O$_2$/O$_3$ in the presence of ethyl acetate or methanolmethylene chloride to form 2,3-O-isopropylidene-D-erythruronolactone 1;
  b. treating said 2,3-O-isopropylidene-D-erythruronolactone 1 with NaBH$_4$ at room temperature and in the presence of methanol to form 2,3-O-isopropylidene-L-erythrolactone 50; and
  c. treating said 2,3-O-isopropylidene-L-erythrolactone 50 with DIBAL solution in the presence of CH$_2$Cl to yield 2,3-O-isopropylidene-L-erythrose 17.

8. A method for producing 2,3-O-isopropylidene-L-erythrose 17, useful as an intermediate compound, said method comprising:
  a. treating (2S,3S)-2,3-O-isopropylidene-1-chlorocylohexa-4,6-diene with ozone in the presence of methanol-methylene chloride; and
  b. adding to the reaction of step a) NaBH$_4$ and NH$_4$Cl to yield 2,3-O-isopropylidene-L-erythrose 17.

9. A method for producing 2,3-O-isopropylidene-D-erythrose 18 useful as an intermediate compound, said method comprising:

a. treating a hydroxylactone 1 with triphenylmethyl-phosphonium bromide in the presence of THF, purifying such mixture to yield (2S,3S)-2,3-O-iso-propylidene-4-pentenoic acid 12;

b. treating said pentenoic acid 12 with LAH in the presence of ether to yield a pentenol, (2R,3S)-2,3-O-isopropylidene-4-pentenol 16;

c. subjecting said pentenol 16 to ozonolysis in the presence of CH₂Cl₂ and adding dimethyl sulfide to yield a lactol, 2,3-O-isopropylidene-D-erythrose 18 provided that steps (a), (b) and (c) above can be carried out sequentially without isolation of the product of each step.

10. A method for producing (1R,4S,5R,6S)-1-chloro-7,8-dioxa-5,6-di-O-isoproylidenebicyclo[2.2]oct-2-ene 21, said method comprising reacting tetraphenylporphine in chloroform with an acetonide, AA, 2,3-O-iso-propylidene-L-erythrose in the presence of oxygen and removing the solvent to afford the endoperoxide 21.

11. A method for producing (4R,5S,6R)-4-hydroxy-5,6-di-O-isopropylidenecyclohex-2-en-1-one 8 which comprises treating the endoperoxide 21 produced by the method of claim 10 with thiourea in the presence of MeOH.

12. A method for producing an epoxide useful as an intermediate, said epoxide having the formula:

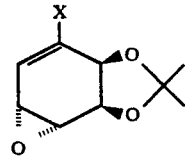
(2)

(wherein X=halogen), said method comprising subjecting an acetonide of the formula:

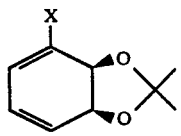

(wherein X =halogen)
to epoxidation with MCPBA in the presence of CH₂Cl₂.

13. A method of claim 12 wherein X is Cl and the resulting epoxide is (1R,4S,5S,6R)-3-chloro-4,5-di-O-isopropylidene-7-oxa-bicyclo[4.1.0]hept-2-ene 2a.

14. A method of claim 12 wherein X is Br and the resulting epoxide is (1R,4S,5S,6R)-3-Bromo-4,5-di-O-isopropylidene-7-oxa-bicyclo[4.1.0]hept-2-ene 2b.

15. A method for producing a diol useful as an intermediate compound, said method comprising subjecting an acetonide of the formula:

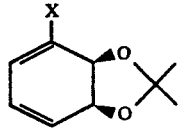

(wherein X=halogen) to dioxygenation with OsO₄ in the presence of N-methylmorpholine-N-oxide to yield a diol of the formula:

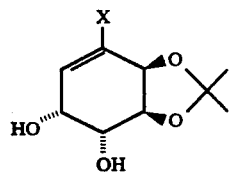

wherein X=halogen.

16. A method of claim 15 wherein X is Cl and the resulting diol is (1R,2R,3S,4S)-5-chloro-1,2-dihydroxy-3,4-di-O-iso-propylidenecyclohex-5-ene 3a.

17. A method of claim 16 wherein X is Br and the resulting diol is (1R,2R,3S,4S)-5-Bromo-1,2-dihydroxy-3,4-di-O-isopropylidenecyclohex-5-ene 3b.

18. A method for producing a diol of the formula:

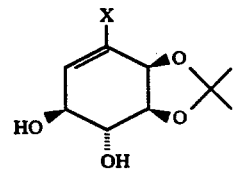

wherein X=halogen,
which comprises adding to the epoxide product produced by the method of claim 12 KOH in the presence of DMSO.

19. A method for producing (1S,2R,3S,4S)-5-Bromo-1,2-dihydroxy-3,4-di-O-isopropylidene cyclohex-5-ene which comprises adding to the (1R,4S,5S,6R)-3-Bromo-4,5-di-O-isopropylidene-7-oxa-bicyclo [4.1.0] hept-2-ene 2b produced by the method of claim 14 KOH in the presence of DMSO.

20. A method for making L-Ribonolactone 19, useful as an intermediate, said process comprising subjecting an olefinic acid of the formula:

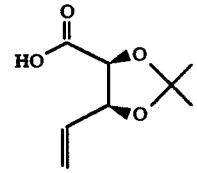

to dioxygenation in the presence of acetone and water to yield L-ribonolactone after deprotection of the acetonide.

21. An intermediate compound useful in the synthesis of chiral synthons, said intermediate compound being selected from the group consisting of: (1R,4S,5R,6S)-1-Choro-7,8-dioxa-5,6-di-O-isopropylidenebicyclo [2.2.2] oct-2-ene; (1R,4S,5R,6S)-1-Bromo-7,8-dioxa-5,6-di-O-isopropylidenebicyclo [2.2.2] oct-2-ene; (4R,5S,6R)-4-hydroxy-5,6-di-O-isopropylidenecyclohex-2-en-1-one; (1R,4S,5S,6R)-3-Chloro-4,5-di-O-isopropylidene-7-oxa-bicyclo [4.1.0] hept-2-ene; (1R,4S,5S,6R)-3-Bromo-4,5-di-O-isopropylidene-7-oxa-bicyclo [4.1.0 ] hept-2-ene; (1R,2R,3S,4S)-5-Chloro-1,2-dihydroxy-3,4-di-O-isopropylidenecyclohex-5-ene; (1R,2R,3S,4S)-5-Bromo-1,2-dihydroxy-3,4-di-O-isopropylidenecyclohex-5-ene; (1S,2R,3S,4S)-5-Bromo-1,2-dihydroxy-3,4-di-O-isopropylidenecyclohex-5-ene; (1S,2R,3S,4S)-5-Chloro-1,2-dihydroxy-3,4-di-O-isopropylidenecyclohex-5-ene;

(2S,3S)-2,3-O-Isopropylidene-1-chloroclohexa-4,6diene; and 2,3-O-Isopropylidene-D-erythruronolactone.

22. A method for producing L-erythrose, said method comprising:
   a. subjecting (+)-cis-2,3-dihydroxy-1-chloro-cyclohexa-4,6-diene to ozonolysis;
   b. reducing the product of said ozonolysis with sodium borohydride to form 2,3-O-isopropylidene-L-erythrose; and
   c. deprotecting said 2,3-O-isopropylidene-L-erythrose to form L-erythrose.

23. A method for producing L-erythrose, said method comprising:
   a. treating (+)-cis-2,3-dihydroxy-1-chloro-cyclohexa-4, 6-diene with p-toluenesulfonic acid in the presence of 2, 2-dimethoxypropane to form (2R,3S)-2, 3-isopropylidene-1-chloro-cyclohexa-4, 6-diene;
   b. subjecting said (2R,3S)-2,3-isopropylidene-1-chloro-cyclohexa-4, 6-diene to ozonolysis followed by cyclization of the product of said ozonolysis to form 2,3-O-isopropylidene-D-erythruronolactone;
   c. reducing said 2,3-O-isopropylidene-D-erythruronolactone in the presence of sodium borohydride to produce sodium (S,S)-2,3-dihydroxy-2,3-O-isopropylidene-4-hydroxy-butanoate;
   d. cyclizing said sodium (S,S)-2,3-dihydroxy-2,3-O-isopropylidene-4-hydroxybutanoate in the presence of iodomethane to form 2,3-O-isopropylidene-L-erythrono-1, 4-lactone;
   e. treating said 2,-3-O-isopropylidene-L-erythrono-1, 4-lactone-with DIBAL solution to form 2,3-O-isopropylidene-L-erythrose; and
   f. deprotecting said 2,3-O-isopropylidene-L-erythrose to form L-erythrose.

24. A method of producing D-erythrose, said method comprising:
   a. treating (+)-cis-2, 3-dihydroxy-1-chloro-cyclohexa-4, 6-diene with p-toluenesulfonic acid in the presence of 2, 2-dimethoxypropane to form (2R,3S)-2, 3-isopropylidene-1-chloro-cyclohexa-4, 6-diene;
   b. subjecting said (2R,3S)-2,3-isopropylidene-1-chloro-cyclohexa-4, 6-diene to ozonolysis followed by cyclization of the product of said ozonolysis to form 2, 3-O-isopropylidene-D-erythruronolactone;
   c. subjecting said 2,3-O-isopropylidene-D-erythruronolactone to olefination to form (2S,3S)-dihydroxy-2, 3-O-isopropylidene-4-pentenoic acid;
   d. reducing said (2S,3S)-dihydroxy-2, 3-O-isopropylidene-4-pentenoic acid in the presence of LAH to form (2R,3S)-2, 3-O-isopropylidene-4-penten-1,2,3-triol;
   e. subjecting said (2R,3S)-2, 3-O-isopropylidene-4-penten-1,2,3-triol to ozonolysis followed by cyclization of the product of said ozonolysis to form 2, 3-O-isopropylidene-D-erythrose; and
   f. deprotecting said 2, 3-O-isopropylidene-D-erythrose to form D-erythrose.

25. A method of producing L-ribonic gamma lactone, said method comprising:
   a. treating (+)-cis-2,3-dihydroxy-1-chloro-cyclohexa-4,6-diene with p-toluenesulfonic acid in the presence of 2,2-dimethoxypropane to form (2R,3S)-2,3-isopropylidene-1-chloro-cyclohexa-4,6-diene;
   b. subjecting said (2R,3S)-2,3-isopropylidene-1-chloro-cyclohexa-4,6-diene to ozonolysis followed by cyclization of the product of said ozonolysis to form 2,3-O-isopropylidene-D-erythruronolactone;
   c. subjecting said 2,3-O-isopropylidene-D-erythruronolactone to olefination to form (2S,3S)-dihydroxy-2,3-O-isopropylidene-4-pentenoic acid;
   d. subjecting said (2S,3S)-dihydroxy-2,3-O-isopropylidene-4-pentenoic acid to hydroxylation to form an intermediate diol which cyclizes to form the L-ribonic gamma-lactone.

26. A method for making (2S,3S)-2,3-O-Isopropylidene-1-chlorocyclohexa-4,6-diene useful as an intermediate, said method comprising: reacting a dienediol A with a mixture of 2,2-dimethoxypropane-acetone, in the presence of p-toluenesulfonic acid to yield (2S,3S)-2,3-O-Isopropylidene-1-chlorocyclohexa-4,6-diene.

27. A method for making 2,3-O-Isopropylidene-D-erythruronolactone, useful as an intermediate, said method comprising reacting (2S,3S)-2,3-O-Isopropylidene-1-chlorocyclohexa-4,6-diene, with ethyl acetate and ozone to yield 2,3-O-Isopropylidene-D-erythruronolactone.

28. A method for making (2S,3S)-2,3-O-Isopropylidene-4-pentenoic acid useful as an intermediate, said method comprising:
   a. reacting triphenylmethyl phosphorium bromide in THF with n-BuLi; or
   b. adding 2,3-O-Isopropylidene-D-erythruronolactone in THF with stirring, to yield (2S,3S)-2,3-O-Isopropylidene-4-pentenoic acid.

29. A method for producing (2R,3S)-2,3-O-Isopropylidene-4-pentenol which comprises reacting the (2S,3S)-2,3-O-Isopropylidene-4-pentenoic acid produced by the method of claim 28 in ether, with LAH with stirring and quenching such reaction mixture with water and aqueous NaOH.

* * * * *